US012788304B2

(12) United States Patent
Ho et al.

(10) Patent No.: US 12,788,304 B2
(45) Date of Patent: Nov. 10, 2026

(54) BODY BALANCE MEASURING DEVICE

(71) Applicant: KOREA RESEARCH INSTITUTE OF STANDARD AND SCIENCE, Daejeon (KR)

(72) Inventors: Kim Jong Ho, Daejeon (KR); Song Han Wook, Daejeon (KR); Woo Sam Yong, Daejeon (KR)

(73) Assignee: KOREA RESEARCH INSTITUTE OF STANDARD AND SCIENCE, Daejeon (KR)

( * ) Notice: Subject to any disclaimer, the term of this patent is extended or adjusted under 35 U.S.C. 154(b) by 306 days.

(21) Appl. No.: 18/641,659

(22) Filed: Apr. 22, 2024

(65) Prior Publication Data

US 2025/0152081 A1 May 15, 2025

(30) Foreign Application Priority Data

Nov. 15, 2023 (KR) ........................ 10-2023-0158012

(51) Int. Cl.
*A61B 5/00* (2006.01)
*A61B 5/103* (2006.01)

(52) U.S. Cl.
CPC .......... *A61B 5/4023* (2013.01); *A61B 5/1036* (2013.01); *A61B 2562/0261* (2013.01)

(58) Field of Classification Search
CPC ....... A61B 5/0252; A61B 5/09; A61B 5/1036; A61B 5/1116; A61B 5/1121;
(Continued)

(56) References Cited

U.S. PATENT DOCUMENTS 3,640,130 A * 2/1972 Spescha .................. G01L 5/167
73/862.043
4,398,429 A * 8/1983 Cook .................... G01L 1/2237
600/595
(Continued)

FOREIGN PATENT DOCUMENTS

CN 107095674 A * 8/2017 ............. G01G 19/44
CN 111544830 A * 8/2020 ....... A63B 21/00181
(Continued)

OTHER PUBLICATIONS

CN107095674 and English Machine Translation (Year: 2017).*
(Continued)

*Primary Examiner* — Adam J Eiseman
(74) *Attorney, Agent, or Firm* — Hoffmann & Baron, LLP

(57) ABSTRACT

A body balance measuring device and a correction system using the same allow continuous exercise of the elderly, patients, etc. by measuring body changes, balance changes, etc. after exercise. The body balance measuring device includes: a top plate applied with a weight of a user, and having a top plate step formed on at least a part of a periphery; first, second, third, and fourth force sensors installed at a lower corner region of the top plate; a bottom plate supporting a bottom surface; placement grooves formed to be recessed at regions corresponding to the force sensors, respectively on the bottom plate; and a housing maintaining an interval between the top plate and the bottom plate, and having a housing step shape-customized to the top plate step on a periphery thereof.

11 Claims, 6 Drawing Sheets

(58) Field of Classification Search
CPC .......... A61B 5/4023; A61B 2562/0261; A63B 26/003; A63B 26/0062; A63B 26/0093; G01G 19/44; G01G 19/50; G01G 21/23
See application file for complete search history.

(56) References Cited

U.S. PATENT DOCUMENTS

| | | | | |
|---|---|---|---|---|
| 4,493,220 | A * | 1/1985 | Carignan | G01L 1/225 73/862.635 |
| 4,598,717 | A * | 7/1986 | Pedotti | G06F 3/005 600/592 |
| 5,029,483 | A * | 7/1991 | Gautschi | G01L 1/16 73/862.622 |
| 5,400,661 | A * | 3/1995 | Cook | G01L 5/164 73/862.041 |
| 6,052,114 | A * | 4/2000 | Morifuji | G06F 3/0334 345/158 |
| 6,063,046 | A * | 5/2000 | Allum | A61B 5/1036 600/595 |
| 6,389,883 | B1 * | 5/2002 | Berme | A61B 5/706 73/65.01 |
| 7,955,279 | B2 * | 6/2011 | Berthonnaud | A61B 5/4023 600/595 |
| 8,394,002 | B2 * | 3/2013 | Park | H02P 3/18 482/7 |
| 9,202,386 | B2 * | 12/2015 | Yuasa | G09B 19/00 |
| 9,255,859 | B2 * | 2/2016 | Drueding | A61B 5/7235 |
| 9,480,918 | B2 * | 11/2016 | Hayashi | A63F 13/218 |
| 9,526,451 | B1 * | 12/2016 | Berme | A61B 5/486 |
| 9,814,430 | B1 * | 11/2017 | Berme | A61B 5/0077 |
| 10,506,967 | B2 * | 12/2019 | Guo | G01L 5/00 |
| 10,646,153 | B1 * | 5/2020 | Berme | A61B 5/1036 |
| 10,660,558 | B2 * | 5/2020 | Goble | A61B 5/1036 |
| 11,604,106 | B2 * | 3/2023 | Berme | G01L 1/2206 |
| 11,857,331 | B1 * | 1/2024 | Berme | A61B 5/1038 |
| 12,158,382 | B1 * | 12/2024 | Berme | G01G 21/23 |
| 12,332,133 | B2 * | 6/2025 | Patel | A61B 5/01 |
| 2004/0163855 | A1 * | 8/2004 | Carlucci | A61B 5/4023 177/200 |
| 2005/0119592 | A1 * | 6/2005 | Frank | A61B 5/1036 600/595 |
| 2005/0182341 | A1 * | 8/2005 | Katayama | A61B 5/103 600/592 |
| 2006/0174718 | A1 * | 8/2006 | Morimoto | G01L 5/1627 73/862.044 |
| 2006/0293613 | A1 * | 12/2006 | Fatehi | A61B 5/447 600/595 |
| 2010/0023293 | A1 * | 1/2010 | Walthert | G01G 23/3735 702/101 |
| 2011/0212814 | A1 * | 9/2011 | Gehris, Jr. | A61B 5/4023 482/142 |
| 2012/0271565 | A1 * | 10/2012 | Berme | A61B 5/1036 702/41 |
| 2016/0113584 | A1 * | 4/2016 | Galasso | A61B 5/1036 600/592 |
| 2019/0232113 | A1 * | 8/2019 | Zets | A61B 5/1128 |
| 2020/0187842 | A1 * | 6/2020 | Vayatis | G16H 50/30 |
| 2020/0289035 | A1 * | 9/2020 | Sato | A63B 22/20 |
| 2022/0003592 | A1 * | 1/2022 | Kobayashi | A61B 5/1036 |
| 2023/0043160 | A1 * | 2/2023 | An | A63B 26/003 |
| 2023/0131793 | A1 * | 4/2023 | Guess | A61B 5/0077 600/595 |
| 2024/0277256 | A1 * | 8/2024 | Aljamaan | A61B 5/112 |
| 2025/0362189 | A1 * | 11/2025 | Heracleous | G01L 5/162 |

FOREIGN PATENT DOCUMENTS

| | | | | | |
|---|---|---|---|---|---|
| KR | 10-2007-0073566 | A | | 12/2007 | |
| KR | 10-2009-0003822 | A | | 1/2009 | |
| KR | 20130122343 | A | * | 11/2013 | A61B 5/4023 |
| KR | 10-2013-0122343 | A | | 3/2014 | |
| KR | 10-2017-012569 | A | | 11/2017 | |
| KR | 101786846 | B1 | * | 11/2017 | A63B 24/0087 |
| KR | 10-1980378 | B1 | | 8/2019 | |
| KR | 10-2019-0118526 | A | | 10/2019 | |
| KR | 20200069402 | A | * | 6/2020 | A61B 5/4869 |
| KR | 20220055310 | A | * | 5/2022 | A61B 5/1036 |
| KR | 20220121927 | A | * | 9/2022 | A61B 5/1124 |
| KR | 10-2022-0121927 | A | | 1/2023 | |
| KR | 20250015359 | A | * | 2/2025 | A61B 5/7445 |

OTHER PUBLICATIONS

CN111544830 and English Machine Translation (Year: 2020).*
KR101786846 and English Machine Translation (Year: 2017).*
KR20130122343 and English Machine Translation (Year: 2013).*
KR20200069402 and English Machine Translation (Year: 2020).*
KR20220055310 and English Machine Translation (Year: 2022).*
KR20220121927 and English Machine Translation (Year: 2022).*
KR20250015359 and English Machine Translation (Year: 2025).*
Korea Ministry of Intellectual Property, Korean Application No. 10-2023-0158012, First Office Action, Mar. 16, 2026, 15 pages.

* cited by examiner

BODY BALANCE MEASURING DEVICE

CROSS-REFERENCE TO RELATED APPLICATIONS

This application claims the priority of Korean Patent Application No. 10-2023-0158012 filed on Nov. 15, 2023, in the Korean Intellectual Property Office, the disclosure of which is incorporated herein by reference.

BACKGROUND

Field

The present disclosure relates to balance measurement of a body, and more particularly, to a body balance measuring device which allows continuous exercise of the elderly, patients, and the like by measuring body changes, balance changes, and the like after exercise.

Description of the Related Art

In recent years, there are many cases in various forms of exercise in gyms, sports clubs, rehabilitation hospitals, homes and the like. For example, at home, exercise alone is called home training, and there are personal training (PT) and group exercise (GX), and some exercises are aimed at rehabilitation training or rehabilitation treatment.

The exercises are especially necessary for the elderly, patients, housewives, and elderly people, and the effect is more effective when the exercise is periodic and continuous.

However, the conventional exercise equipment was often specialized for professional exercise equipment for certain areas of a body, and it was necessary to move to a separate measuring device in order to measure changes or balance in the body after exercise. The balance of such a body includes weight, changes in left-right or front-rear movement of the center of gravity, body fat, body temperature, heart rate, blood pressure, left and right balance, and the like.

In particular, in the case of elderly people or those who live alone, it is difficult for them to go out, so although home training is suitable, it is not settled due to difficulty in arousing interest, lack of professional knowledge, and low motivation.

On the other hand, the conventional body measuring device was completed by accurately calibrating each sensor and then attached to a set or housing. However, due to the fact that the production error or assembly error was prone to occur during the manufacturing process, the completed measuring device could not show accurate performance. To this end, in related art, the sensor had to be attached very carefully, or it was necessary to pay a lot of attention to dimension management and quality management of a mechanism. Such a production method often resulted in increased manufacturing costs, increased defect rates, decreased precision, and the like.

SUMMARY

Accordingly, the present disclosure is contrived to solve the problem, and an object of the present disclosure is to provide a body balance measuring device and a correction system using the same which may easily measure a balance change of a body after exercise.

Another object of the present disclosure is to provide a body balance measuring device and a correction system using the same which may manufacture a balance measuring device configured by an expensive system in the related art at low cost and easily correct the balance measuring device.

However, technical objects to be achieved by the present disclosure are not limited to the aforementioned technical objects, and other technical objects not described above may be evidently understood by a person having ordinary skill in the art to which the present disclosure pertains from the following description.

According to an aspect of the present disclosure, there is provided a body balance measuring device which includes: a top plate 210 applied with a weight of a user, and having a top plate step 215 formed on at least a part of a periphery; at least two electrode units installed on the top plate 210 and measuring impedance of soles; first, second, third, and fourth force sensors 190, 200, 170, and 180 installed at a lower corner region of the top plate 210; a bottom plate 220 supporting a bottom surface; placement grooves 230 formed to be recessed at regions corresponding to the force sensors, respectively on the bottom plate 220; and a housing 150 maintaining an interval between the top plate 210 and the bottom plate 220, and having a housing step 155 shape-customized to the top plate step 215 on a periphery thereof.

Further, the first, second, third and fourth force sensors 190, 200, 170, and 180 include a dummy bridge 300 including first and second resistances, a first half bridge 250 connected to the dummy bridge 300, and including third and fourth resistances, a second half bridge 260 connected to the dummy bridge 300, and including fifth and sixth resistances, a fourth half bridge 280 connected to the dummy bridge 300, and including seventh and eighth resistances, and a third half bridge 270 connected to the dummy bridge 300, and including ninth and tenth resistances.

In addition, the body balance measuring device is set as a first measuring device 100*a*, and further includes a second measuring device 100*b* installed in the vicinity of the first measuring device 100*b*→100*a* and having the same configuration as the first measuring device 100*b*→100*a*.

Further, a vibration motor 240 is further provided at a lower portion of the top plate 210.

In addition, the body balance measuring device further includes: a correction device 500 including a base 310 on which the body balance measuring device is placed, first, second, third, and fourth reference sensors 320, 330, 340, and 350 installed on the base 310 to correspond to the first, second, third, and fourth force sensors 190, 200, 170, and 180, respectively, and a flat plate 360 and a curvature transfer unit 370 installed between each force sensors and each reference sensors, and output signals of the first force sensor 190 and the first reference sensor 320 are compared, output signals of the second force sensor 200 and the second reference sensor 330 are compared, output signals of the third force sensor 170 and the third reference sensor 340 are compared, and output signals of the fourth force sensor 180 and the fourth reference sensor 350 are compared to simultaneously correct the first, second, third, and fourth force sensors 190, 200, 170, and 180.

Further, an output signal slope of the first force sensor 190 is corrected to match an output signal of the first reference sensor 320, an output signal slope of the second force sensor 200 is corrected to match an output signal of the second reference sensor 330, an output signal slope of the third force sensor 170 is corrected to match an output signal of the third reference sensor 340, and an output signal slope of the fourth force sensor 180 is corrected to match an output signal of the fourth reference sensor 350.

In addition, the body balance measuring device further includes: a mechanism 440 which the user on the top plate 210 may stand upright and grip; a connector 160 electrically connecting the measuring device and the mechanism 440; a plurality of distance sensors 420 distributed and installed on the mechanism 440, and measuring a distance from the user; and a controller 450 measuring a body balance of the user based on the output signals of the first, second, third, and fourth force sensors 190, 200, 170, and 180, and the distance sensor 420.

Further, the plurality of distance sensors 420 are distributed and installed on a vertical plane in a waist height region of the user.

In addition, a monitor 410 displaying an operation result of the controller 450 is further provided at an upper portion of the mechanism 440.

Further, the monitor 410 may further include a camera 480 for measuring a body temperature or blood pressure of the user.

In addition, the mechanism may further include a pair of handles 430 which the user may stand upright and grip, and a handle electrode 435 provided on the handle 430 and measuring impedance of palms.

Further, balance measuring device further includes: a bottom plate step 224 formed on a circumference of the bottom plate 220; and a lower step 157 maintaining an interval between the bottom plate 220 and the housing 150, and formed on a periphery of the housing 150 and shape-customized to the bottom plate step 224.

Further, according to another aspect of the present disclosure, provided is a body balance measuring device which includes: a first top plate 210*a* applied with one-side leg weight of a user, and having a top plate step 215 formed on at least a part of a periphery; a second top plate 210*b* applied with the other-side leg weight of the user, and a top plate step 215 formed on at least a part of the periphery; first, second, third, and fourth force sensors 190, 200, 170, and 180 installed at a lower corner region of the first top plate 210*a*; fifth, sixth, seventh, and eighth force sensors 195, 205, 175, and 185 installed at a lower corner region of the second top plate 210*b*; a first bottom plate 220*a* supporting a bottom surface at a lower portion of the first top plate 210*a* and having a bottom plate step 224 on a periphery thereof; a second bottom plate 220*b* supporting a bottom surface at a lower portion of the second top plate 210*b* and having a bottom plate step 224 on a periphery thereof; placement grooves 230 formed to be recessed at regions corresponding to the force sensors, respectively on the first and second bottom plates 220*a* and 220*b*; a housing 150 having a housing step 155 corresponding to the top plate step 215 on an upper periphery while maintaining intervals with the first and second top plates 210*a* and 210*b*, and having a lower step 157 corresponding to the bottom plate step 224 on a lower periphery while maintaining intervals with the first and second bottom plates 220*a* and 220*b*; an upper frame 510 positioned while maintaining an interval between the first and second top plates 210*a* and 210*b*, and having a frame step 530 corresponding to the top plate step 215; and a lower frame 520 positioned while maintaining an interval between the first and second bottom plates 220*a* and 220*b*, and having a lower step 540 corresponding to the bottom plate step 224.

According to an exemplary embodiment of the present disclosure, a user may measure a balance change of a body immediately after exercise. Through this, the users may experience an effect of the exercise and gain sufficient motivation to continue doing the exercise on their own.

In addition, a change in the body according to the exercise may be quickly checked without the help of experts.

In addition, there is an advantage that there is no limit to the type of exercise because a measuring unit of the present disclosure may be incorporated into various exercise equipment (e.g., treadmills, stepper, bicycles, etc.).

In addition, there is convenience in that the user individually can purchase a measurement system that is inexpensive and shows accurate measurement performance and can be used at home.

However, effects which can be obtained in the present disclosure are not limited to the aforementioned effects and other unmentioned effects will be clearly understood by those skilled in the art from the following description.

BRIEF DESCRIPTION OF THE DRAWINGS

The accompanying drawings of this specification exemplify a preferred exemplary embodiment of the present disclosure, the technical spirit of the present disclosure will be more clearly understood in conjunction with a detailed description to be described below, and thus it will be understood that the present disclosure is not limited to only contents illustrated in the accompanying drawings, in which.

DETAILED DESCRIPTION OF THE PREFERRED EMBODIMENT

Hereinafter, exemplary embodiments of the present disclosure will be described in detail so as to be easily implemented by those skilled in the art, with reference to the accompanying drawings. However, a description of the present disclosure is merely an exemplary embodiment for a structural or functional description and the scope of the present disclosure should not be construed as being limited by exemplary embodiments described in a text. That is, since the exemplary embodiment can be variously changed and have various forms, the scope of the present disclosure should be understood to include equivalents capable of realizing the technical spirit. Further, since a specific exemplary embodiment should not include all objects or effects or include only the effect, it should not be understood that the scope of the present disclosure is limited by the object or effect.

Meanings of terms described in the present disclosure should be understood as follows.

The terms "first," "second,", and the like are used to differentiate a certain component from other components, but the scope of should not be construed to be limited by the terms. For example, a first component may be referred to as a second component, and similarly, the second component may be referred to as the first component. It should be understood that, when it is described that a component is "connected to" another component, the component may be directly connected to another component or a third component may be present therebetween. In contrast, it should be understood that, when it is described that a component is "directly connected to" another component, it is understood that no component is present between the component and another component. Meanwhile, other expressions describing the relationship of the components, that is, expressions such as "between" and "directly between" or "adjacent to" and "directly adjacent to" should be similarly interpreted.

It is to be understood that the singular expression encompasses a plurality of expressions unless the context clearly dictates otherwise and it should be understood that term "include" or "have" indicates that a feature, a number, a step, an operation, a component, a part or the combination thereof described in the specification is present, but does not exclude a possibility of presence or addition of one or more other features, numbers, steps, operations, components, parts or combinations thereof, in advance.

If it is not contrarily defined, all terms used herein have the same meanings as those generally understood by those skilled in the art. Terms which are defined in a generally used dictionary should be interpreted to have the same meaning as the meaning in the context of the related art, and are not interpreted as an ideal meaning or excessively formal meanings unless clearly defined in the present disclosure.

Configuration of Exemplary Embodiment

Figure 1:
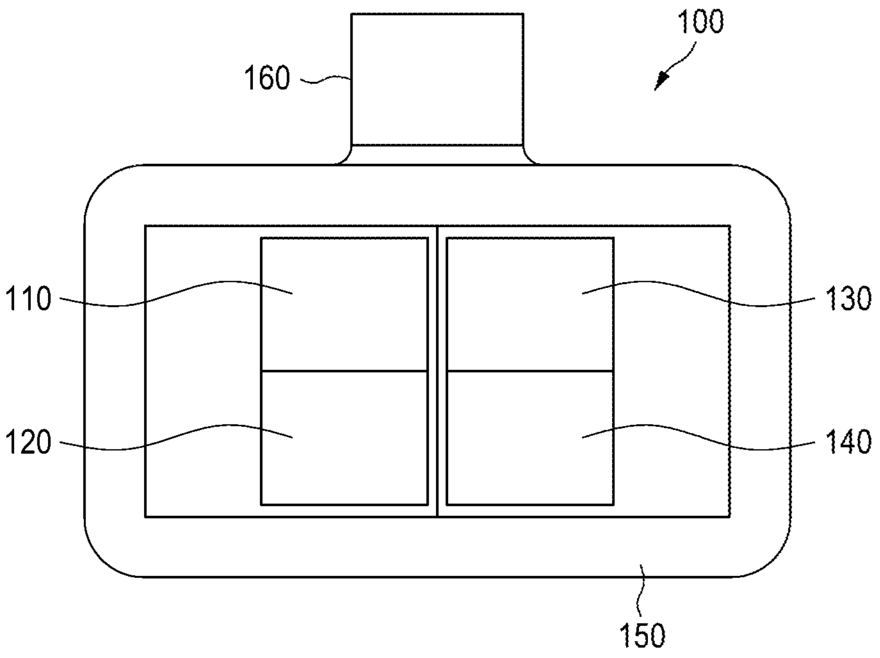
FIG. 1 is a plan view of a measuring device 100 in a body balance measuring device according to the present disclosure.
Figure 2A:
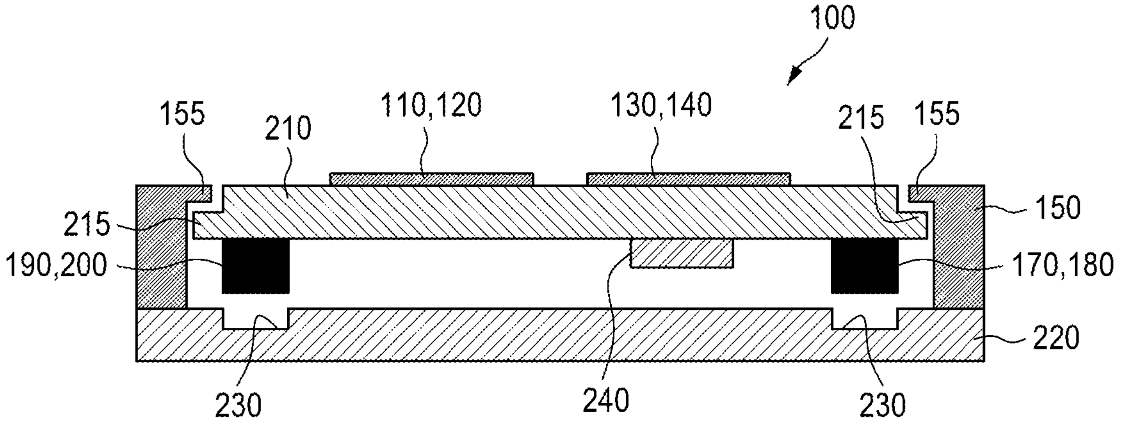
FIG. 2A is a front cross-sectional view of the measuring device 100 illustrated in FIG. 1.

FIG. 1 is a plan view of a measuring device 100 in a body balance measuring device according to the present disclosure, and FIG. 2A is a front cross-sectional view of the measuring device 100 illustrated in FIG. 1. As illustrated in FIGS. 1 and 2A, the body balance measuring device 100 has a rectangular top plate 210, and includes first, second, third and fourth force sensors 190, 200, 170, and 180 for respective corner regions of a lower surface of the top plate 210, respectively.

The first, second, third, and fourth force sensors 190, 200, 170, and 180 are all installed in the same form, and output an electric signal which is in proportion to an applied load. A representative example of the first, second, third, and fourth force sensors 190, 200, 170, and 180 may become a load cell. In the exemplary embodiment of the present disclosure, four force sensors are used, but by symmetrically placing six and eight force sensors, it is also possible to measure a more accurate balance.

In addition, an electrode unit includes first and second electrode units 110 and 120 dividing and measuring an impedance of a left sole of a user, and third and fourth electrode units 130 and 140 dividing and measuring an impedance of a right sole of the user.

The top plate 210 as a member onto which the user steps is manufactured by metal, synthetic resin (e.g., plastic, acrylic, etc.), tempered glass, and the like to sufficiently withstand a weight. A top plate step 215 is formed around a periphery of the top plate 210, which enables the top plate 210 to be movable up and down only in a housing 150, and prevents the top plate 210 from being lifted out of the housing 150. In addition, a housing step 155 is configured to be also formed on an upper inner periphery of the housing 150 to be in contact with the top plate step 215.

A bottom plate 220 has sufficient rigidity for accurate measurement even if the bottom plate 220 is uneven or lifted. The bottom plate 220 may be made of the same material as the top plate 210.

A placement groove 230 is a groove which is recessed on an upper surface of the top plate 220, and is formed to correspond to each of a location and a size of the first, second, third, and fourth force sensors 190, 200, 170, and 180. Accordingly, when a user steps on the top plate 210, a lower end of the force sensor is in contact with the bottom plate 220 while being inserted into the placement groove 230. That is, the placement groove 230 guides an exact vertical movement of the top plate 210.

A vibration motor 240 may be attached to a lower surface of the top plate 210, and may inform the user of various operation states through vibration. For example, a measurement start, measurement completion, errors, whether balance is normal, and the like may be informed by a cycle and amplitude difference of the vibration. If necessary, a buzzer or speaker may also be added.

Figure 2B:
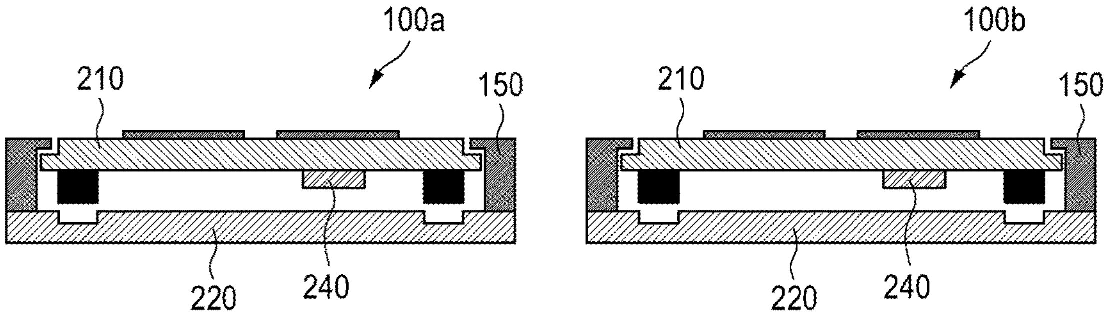
FIG. 2B illustrates a second exemplary embodiment of FIG. 2A.

FIG. 2B illustrates a second exemplary embodiment of FIG. 2A. As illustrated in FIG. 2B, the measuring device 100 illustrated in FIG. 2A becomes a first measuring device 100*a*, and a second measuring device 100*b* having the same configuration as the first measuring device 100*a* is installed to be close to the first measuring device 100*a*. Through this, the first measuring device 100*a* may be a measuring device for a left foot, and the second measuring device 100*b* may become a measuring device for a right foot.

Figure 2C:
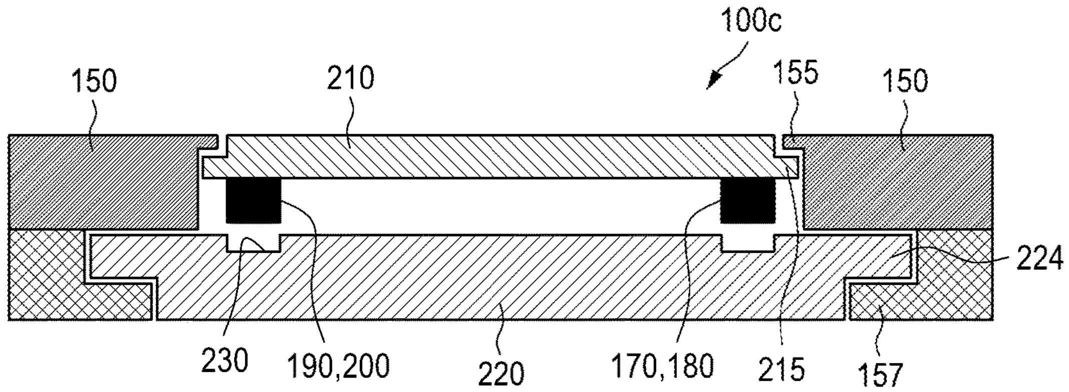
FIG. 2C illustrates a third exemplary embodiment of FIG. 2A.

FIG. 2C illustrates a third exemplary embodiment of FIG. 2A. As illustrated in FIG. 2C, a third measuring device 100*c* has a housing step 155 at an upper portion of the housing 150, and a lower step 157 at a lower portion. Further, the bottom plate 220 maintains a gap with the housing 150, and has a bottom plate step 224 corresponding to a lower step 157 on a circumference thereof. Side force from the housing 150 may be blocked due to an independent structure of the bottom plate 220.

Figure 2D:
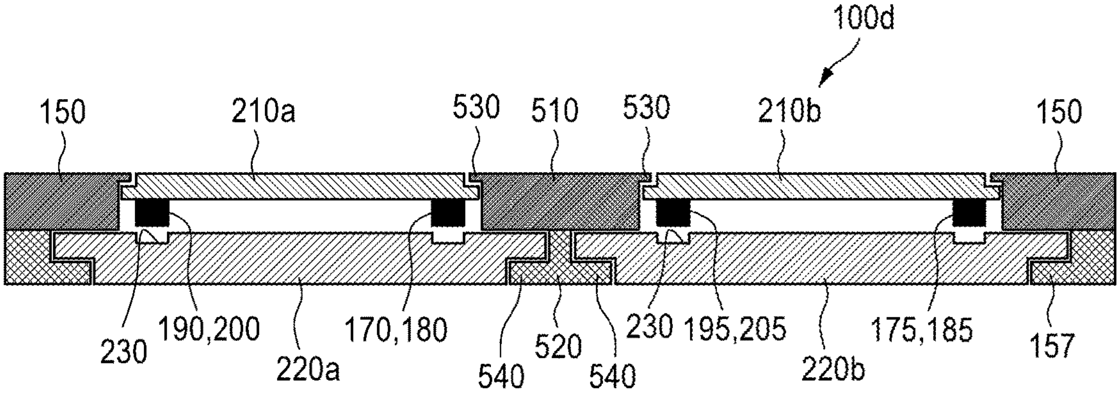
FIG. 2D illustrates a fourth exemplary embodiment of FIG. 2A.

FIG. 2D illustrates a fourth exemplary embodiment of FIG. 2A. As illustrated in FIG. 2D, a fourth measuring device 100*d* has a third measuring device 100*c* for the left foot and a third measuring device 100*c* for the right foot around an upper frame 510 and a lower frame 520. Frame steps 530 are formed at both sides of the upper frame 510, and lower steps 157 are formed at both sides of the lower frame 520.

A top plate step 215 of each of the first and second top plates 210*a* and 210*b* maintains a gap with the upper frame 510, and corresponds to the frame step 530. A bottom plate step 224 of each of the first and second bottom plates 220*a* and 220*b* maintains a gap with the lower frame 520, and corresponds to the lower step 157. Side force from the housing 150, and mutual interference may be blocked due to independent structures of the first and second top plates 210*a* and 210*b* and the first and second bottom plates 220*a* and 220*b*.

Figure 3:
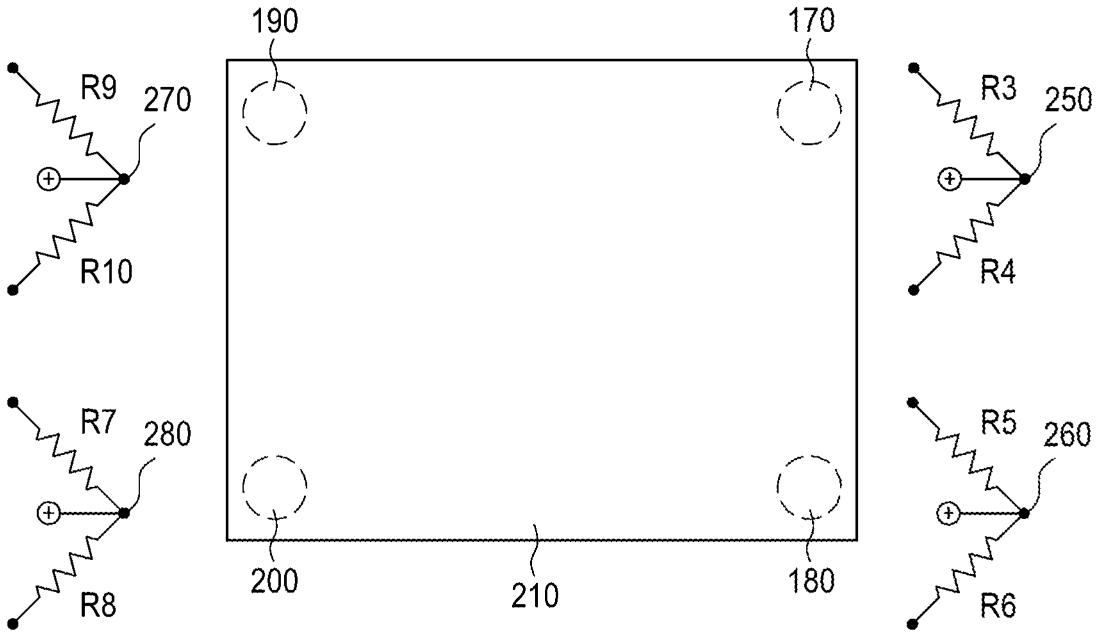
FIG. 3 is a relationship diagram illustrating a schematic measuring device 100 and a half bridge of the present disclosure.
Figure 4:
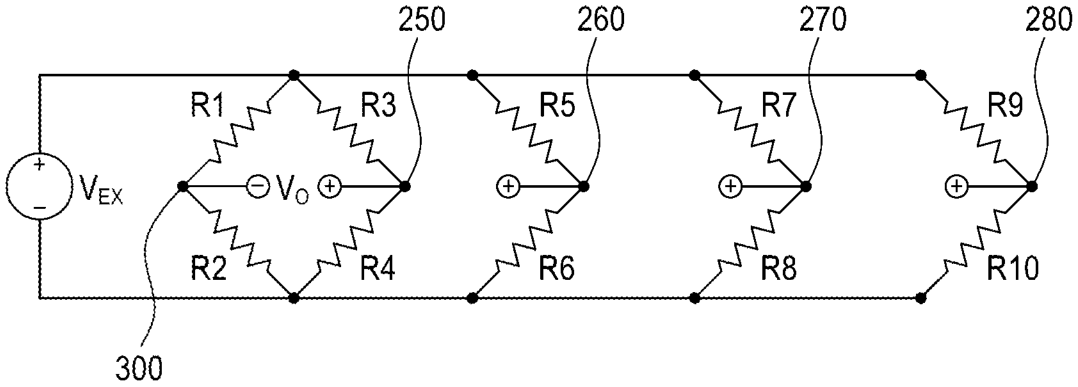
FIG. 4 is a connection circuit diagram of the half bridge illustrated in FIG. 3.

FIG. 3 is a relationship diagram illustrating a schematic measuring device 100 and a half bridge of the present disclosure, and FIG. 4 is a connection circuit diagram of the half bridge illustrated in FIG. 3. As illustrated in FIGS. 3 and 4, a third force sensor 170 is constituted by a dummy bridge 300 in which first and second resistances are connected in series, and a first half bridge 250 which is connected to the dummy bridge 300, and in which third and fourth resistances are connected in series. That is, first, second, third and fourth resistances R1, R2, R3, and R4 constitute a full bridge, and the first and second resistances R1 and R2 are dummy resistances. A reason for such a configuration is that there is a decrease in some sensitivity, but balance measurement is sufficient, and the dummy bridge 300 and the first half bridge 250 may be configured with low cost.

By the same scheme, a fourth force sensor 180 is constituted by a second half bridge 260 which is connected to the dummy bridge 300, and in which fifth and sixth resistances are connected in series. By the same scheme, a second force sensor 200 is constituted by a fourth half bridge 280 which is connected to the dummy bridge 300, and in which seventh and eighth resistances are connected in series. A first force sensor 190 is constituted by a third half bridge 270 which is connected to the dummy bridge 300, and in which ninth and tenth resistances are connected in series.

Accordingly, a controller 450 may measure voltage of the force sensor while sequentially switching the first, second, third, and fourth half bridges 250, 260, 270, and 280.

Figure 6:
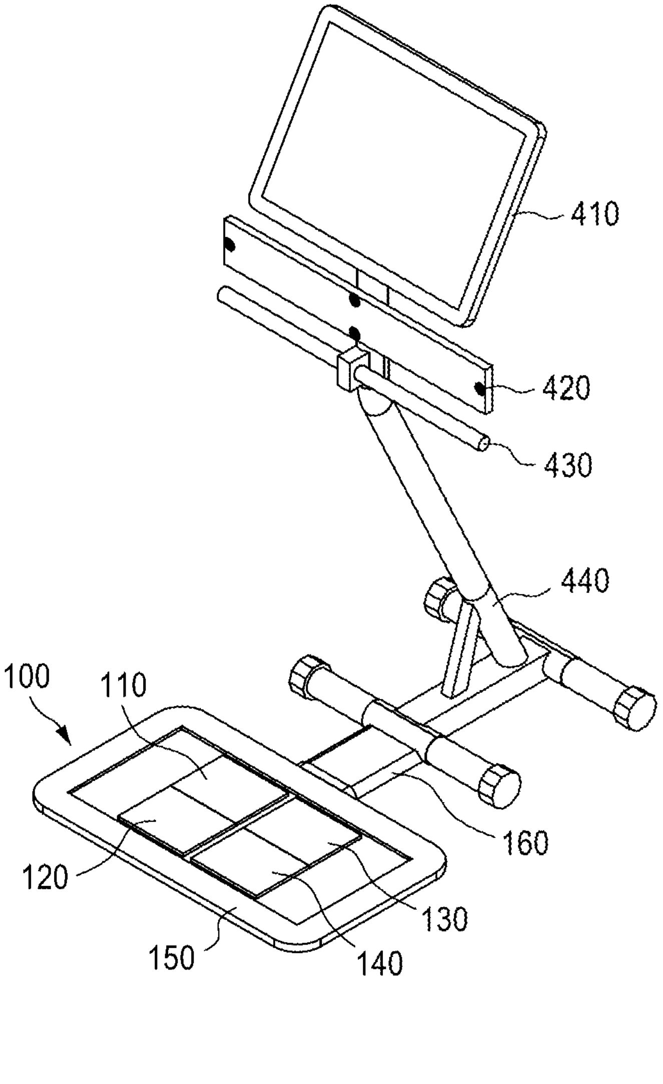
FIG. 6 is a perspective view of the body balance measuring device according to an exemplary embodiment of the present disclosure.
Figure 7:
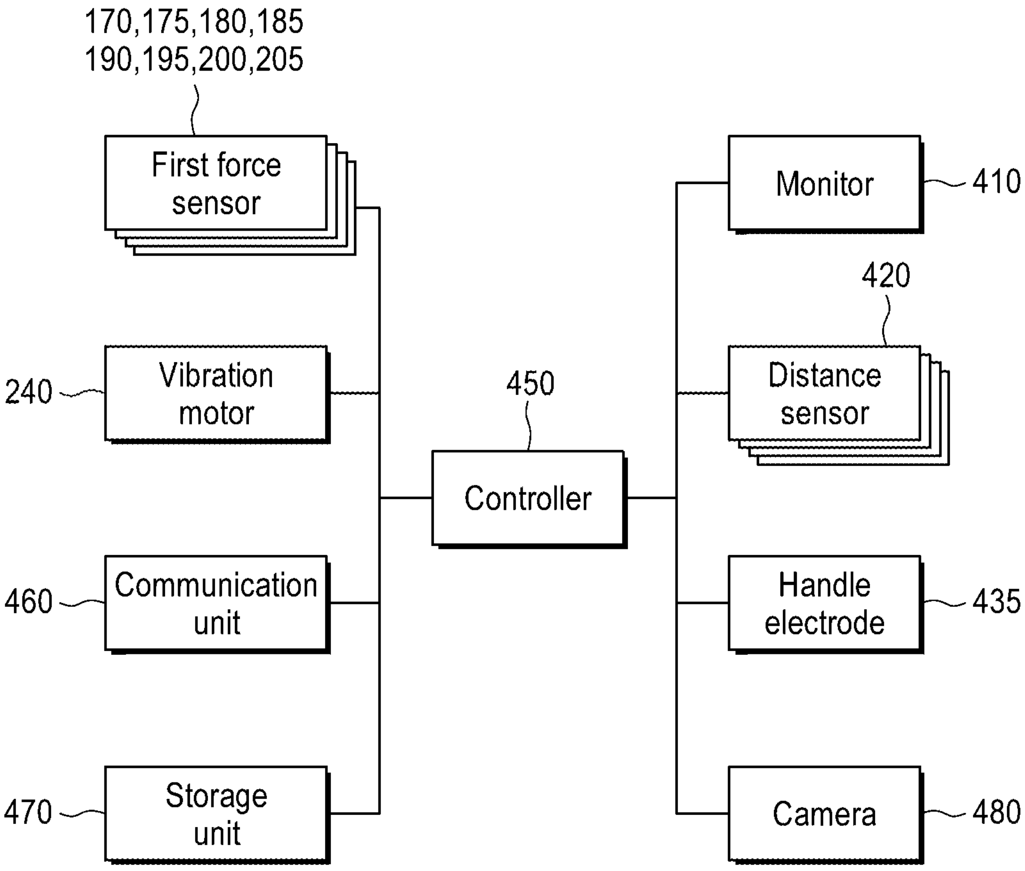
FIG. 7 is a schematic block diagram of the body balance measuring device according to the present disclosure.

FIG. 6 is a perspective view of the body balance measuring device according to an exemplary embodiment of the present disclosure, and FIG. 7 is a schematic block diagram of the body balance measuring device according to the present disclosure. As illustrated in FIGS. 6 and 7, the measuring device 100 and a mechanism 440 are electrically connected by a connector 160.

The mechanism 440 has a handle 430 so that the user who steps onto the measuring device 100 may hold with hands, and has a monitor 410 at an upper portion thereof.

Measured balance information, etc. may be displayed as a graph in the monitor 410, and a small web camera 480 is built in the monitor 410. Optionally, the monitor 410 may be configured as a touch screen for a required input.

The camera 480 shoots a face of the user to measure a body temperature or blood pressure. Such a measurement application is an algorithm known in a cellular phone, etc.

A distance sensor 420 is placed in the form of a vertical plane or a left-right curve under the monitor 410 and corresponds to a waist height region (e.g., belly height) of the user. The distance sensor 420 is a flat rectangular or curved rectangular form, and a total of four distance sensors are placed in respective corner regions and a central region. Through this, the distance sensor 420 may detect left and right movements, up and down movements, front and back movements, and the like of the user.

The handle 430 is extended in a horizontal direction from a lower portion of the distance sensor 430. The handle 430 is gripped by user, which is allowed to keep a stable posture. A pair of handle electrodes 435 is formed in a left handle 430, and a pair of handle electrodes 435 is also formed in a right handle 430. The two pairs of handle electrodes 435 measure an impedance of a palm to measure body fat, heart rate, and the like.

The mechanism 440 has a stable mechanical structure not to fall, and is made of iron, aluminum, or the like. Optionally, exercise equipment such as treadmills, cycling, steppers, etc., may be combined with the mechanism 440.

The controller 450 operates peripheral devices, and measures a body balance of the user based on output signals of the first, second, third, and fourth force sensors 190, 200, 170, and 180. The controller 450 may be a Micom, a CPU of a computer, and an application processor (AP) of the cellular phone.

A communication unit 460 transmits measured balance data and exercise data to an external device. The communication unit 460 includes a Wi-Fi module, a Bluetooth module, an infrared communication module, a wireless LAN module, 3G and 4G communication modules, a ZigBee communication module, an NFC module, a wired LAN, a wired Internet, or the like.

A storage unit 470 is connected to the controller 450 to provide an operating program, an execution program, environmental configuration data, and the like required by the controller 450, and store operation results of the controller 450. The storage unit 210 may be a hard disk, an optical disc, a flash memory, RAM, ROM, EPROM, solid state drive (SSD), compact flash (CF), secure digital (SD), micro secure digital (Micro-SD), mini secure digital (Mini-SD), extreme digital (xD), memory stick, or the like.

As needed, a power supply may be added, which may be driven by a battery by primary battery or secondary battery, and may be driven by an external power supply using an AC power and an adapter.

Operation of Exemplary Embodiment

Hereinafter, an operation of a body balance measuring device according to the present disclosure will be described with reference to the accompanying drawings.

First, a user exercises by using a treadmill or cycling installed in a mechanism 440.

Then, the user steps down from exercise equipment, and steps onto first, second third, and electrode units 110, 120, 130, and 140. In addition, the user holds a handle 430 with hands. In this case, a distance sensor 420 senses front-back and left-right distance changes according to movement of the user.

A monitor 410 may display a guidance operation for measuring a body balance. For example, lifting one foot, half bending knees, bending waist, etc. are displayed so that the user follows the operations.

In the measuring device 100, first, second, third and fourth force sensors 190, 200, 170, and 180 sense respective distributed weights according to a weight of the user, and transmits sensed output signals to a controller 450. In this case, the controller 450 receives the output signals of the first, second, third and fourth force sensors 190, 200, 170, and 180 while sequentially switching first, second, third, and fourth half bridges 250, 260, 270, and 280 in the bridge circuit illustrated in FIG. 4.

The controller 450 represents how much the body balance of the user is changed compared to a body balance before exercise by integrating distribution forces of the first, second, third, and fourth force sensors 190, 200, 170, and 180 and signals of the distance sensor 420. For example, the change of the body balance may be a change range of the center of gravity (unbalanced weight), a left-right balance of the body, front-back swaying of the body, left-right swaying, etc.

Further, impedances of a left foot and a right foot may be measured in the first, second, third, and fourth electrode units 110, 120, 130, and 140, and impedances of a left hand and a right hand are measured in a handle electrode 435. Body fat, muscle mass, body mass index (BMI), obesity, etc., are measured based on the measured impedance values.

Measured body data may be stored in a storage unit 470, and transmitted to a cellular phone of the user or a cell phone of a guardian via a communication unit 460.

Correction of Exemplary Embodiment

Figure 5:
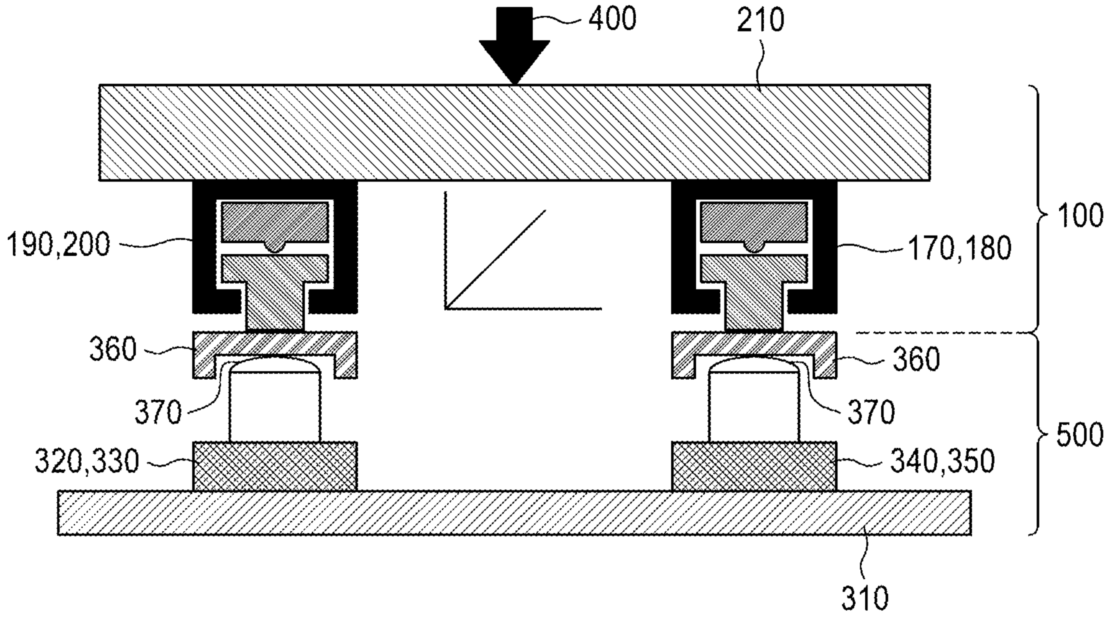
FIG. 5 is a schematic front cross-sectional view of a correction device 500 using the body balance measuring device according to an exemplary embodiment of the present disclosure.

FIG. 5 is a schematic front cross-sectional view of a correction device using the body balance measuring device 500 according to an exemplary embodiment of the present disclosure. As illustrated in FIG. 5, first, the first, second, third, and fourth force sensors 190, 200, 170, and 180 are attached to a top plate 210.

In addition, first, second, third, and fourth reference sensors 320, 330, 340, and 350 are installed in a base 310 to correspond to locations of the first, second, third, and fourth force sensors 190, 200, 170, and 180. The reference sensor as a sensor which becomes a reference of correction outputs an accurate signal. Accordingly, a correction process is a process of adjusting an output signal slope of the force sensor to match an output signal slope of the reference sensor.

A curvature transfer unit 370 and a flat plate 360 are provided at an upper portion of each reference sensor. The curvature transfer unit 370 has a top surface in which a hemispherical curved surface is formed, and is configured in point contact with the flat plate 360. Through this, fine side-direction force or diagonal force also acts only as vertical distribution force.

Then, the assembled top plate 210 and first, second, third, and fourth force sensors 190, 200, 170, and 180 are placed on the flat plate 360. Then, the first force sensor 190, the flat plate 360, the curvature transfer unit 370, and the first reference sensor 320 are formed in a structure of being stacked vertically. By such a scheme, the second, third, and fourth force sensors 200, 170, and 180 are stacked on the second, third, and fourth reference sensors 330, 340, and 350, respectively.

Then, any external force 400 acts on the top plate 210. In a conventional correction scheme, the external force 400 should be an accurate load applied to an accurate location. On the contrary, in the correction system of the exemplary embodiment, the external force 400 may be a different load applied to a different location each time.

The controller 450 corrects an output signal slope of the first force sensor 190 to match an output signal of the first reference sensor 320, corrects an output signal slope of the second force sensor 200 to match an output signal of the second reference sensor 330, corrects an output signal slope of the third force sensor 170 to match an output signal of the third reference sensor 340, and corrects an output signal slope of the fourth force sensor 180 to match an output signal of the fourth reference sensor 350.

Four force sensors are corrected by one correction while the force sensor is assembled as such. As a result, the precision of a product may be greatly increased, manufacturing cost may be lowered, and a production process may be simplified.

Detailed description of the preferred exemplary embodiments of the present disclosure disclosed as described above are provided so as for those skilled in the art to implement and execute the present disclosure. The present disclosure has been described with reference to the preferred exemplary embodiments, but those skilled in the art will understand that the present disclosure can be variously modified and changed without departing from the scope of the present disclosure. For example, those skilled in the art may use the respective components disclosed in the exemplary embodiments by combining the respective components with each other. Therefore, the present disclosure is not limited to the exemplary embodiments described herein, but intends to grant the widest range which is coherent with the principles and new features disclosed herein.

The present disclosure may be embodied in other specific forms without departing from the spirit and essential characteristics of the present disclosure. Accordingly, the aforementioned detailed description should not be construed as restrictive in all terms and should be considered illustrative. The scope of the present disclosure should be determined by rational construing of the appended claims and all modifications within an equivalent scope of the present disclosure are included in the scope of the present disclosure. The present disclosure is not limited to the exemplary embodiments described herein, but intends to grant the widest range which is coherent with the principles and new features presented herein. Further, the claims that are not expressly cited in the claims are combined to form an exemplary embodiment or be included in a new claim by an amendment after the application.

What is claimed is:

1. A body balance measuring device comprising:
- a top plate configured to receive a weight of a user, and having a top plate step formed on at least a part of a periphery;
- first, second, third, and fourth force sensors installed at respective lower corner regions of the top plate;
- a bottom plate supporting a bottom surface;
- recessed placement grooves formed at regions corresponding to the force sensors, respectively on the bottom plate;
- a housing maintaining an interval between the top plate and the bottom plate, and having a housing step shape-customized to the top plate step on a periphery thereof; and
- a correction device comprising:
  - a base on which the body balance measuring device is placed;
  - first, second, third, and fourth reference sensors installed on the base to correspond to the first, second, third, and fourth force sensors, respectively; and
  - a flat plate and a curvature transfer unit installed between each force sensor and each reference sensor,
  - wherein the correction device is configured to compare the output signals of the first force sensor and the first reference sensor, the output signals of the second force sensor and the second reference sensor, the output signals of the third force sensor and the third reference sensor, and the output signals of the fourth force sensor and the fourth reference sensor to simultaneously correct the first, second, third, and fourth force sensors.

2. The body balance measuring device of claim 1, wherein the first, second, third and fourth force sensors include:
- a dummy bridge including first and second resistances;
- a first half bridge connected to the dummy bridge, and including third and fourth resistances;
- a second half bridge connected to the dummy bridge, and including fifth and sixth resistances;
- a fourth half bridge connected to the dummy bridge, and including seventh and eighth resistances; and
- a third half bridge connected to the dummy bridge, and including ninth and tenth resistances.

3. The body balance measuring device of claim 1, wherein the body balance measuring device is set as a first measuring device, and further includes a second measuring device installed in the vicinity of the first measuring device and having the same configuration as the first measuring device.

4. The body balance measuring device of claim 1, wherein the body balance measuring device further comprises at least two electrode units installed on the top plate, and the body balance measuring device is configured to measure impedance through the soles of the user's feet.

5. The body balance measuring device of claim 1, wherein a vibration motor is further provided at a lower portion of the top plate.

6. The body balance measuring device of claim 1, wherein the correction device is further configured to correct an output signal slope of the first force sensor to match the output signal of the first reference sensor, correct an output signal slope of the second force sensor to match the output signal of the second reference sensor, correct an output signal slope of the third force sensor to match the output signal of the third reference sensor, and correct an output signal slope of the fourth force sensor to match the output signal of the fourth reference sensor.

7. The body balance measuring device of claim 1, further comprising:

a mechanism configured to be gripped by a user standing upright on the top plate;

a connector electrically connecting the body balance measuring device and the mechanism;

a plurality of distance sensors distributed and installed on the mechanism, wherein the distance sensors are configured to measure a distance to the user; and a controller configured to measure a body balance of the user based on the corrected output signals of the first, second, third, and fourth force sensors, and the plurality of distance sensors.

8. The body balance measuring device of claim 7, wherein the plurality of distance sensors is distributed and installed on a vertical plane in a waist height region of the user.

9. The body balance measuring device of claim 7, wherein a monitor displaying an operation result of the controller is further provided at an upper portion of the mechanism.

10. The body balance measuring device of claim 9, wherein the monitor further includes a camera for measuring a body temperature or blood pressure of the user.

11. The body balance measuring device of claim 7, wherein the mechanism further includes:

a pair of handles configured for the user to grip, and a pair of handle electrodes provided on the pair of handles configured for measuring impedance through the palms of the user.

* * * * *